United States Patent [19]

Chu et al.

[11] Patent Number: 4,914,252

[45] Date of Patent: Apr. 3, 1990

[54] SELECTIVE OXIDATIVE COUPLING

[75] Inventors: Pochen Chu, West Deptford; Michael E. Landis, Woodbury, both of N.J.

[73] Assignee: Mobil Oil Corporation, New York, N.Y.

[21] Appl. No.: 298,240

[22] Filed: Jan. 12, 1989

Related U.S. Application Data

[63] Continuation of Ser. No. 128,124, Dec. 3, 1987, abandoned.

[51] Int. Cl.$^4$ .............................................. C07C 2/00
[52] U.S. Cl. .................................... 585/500; 585/654; 585/656
[58] Field of Search ............... 585/500, 510, 516, 515, 585/541, 654, 656, 934, 943

[56] References Cited

U.S. PATENT DOCUMENTS

| | | | |
|---|---|---|---|
| 4,308,171 | 12/1981 | Dines | 585/469 X |
| 4,544,785 | 10/1985 | Withers | 585/500 |
| 4,574,038 | 3/1986 | Wan | 204/162 R |
| 4,600,503 | 7/1986 | Angevine | 208/251 |
| 4,629,718 | 12/1986 | Jones | 502/241 |
| 4,670,619 | 6/1987 | Withers | 585/500 |
| 4,791,088 | 12/1988 | Chu | 502/232 |

FOREIGN PATENT DOCUMENTS 0222597 5/1987 European Pat. Off. .

OTHER PUBLICATIONS

T. Ito et al., "Oxidative Dimerization of Methane over a Lithium-Promoted Magnesium Oxide Catalyst", J. Am. Chem. Soc., 1985, 107, 5062–5068.

K. Otsuka et al., "The Catalysts Active and Selective In Oxidative Coupling Of Methane, Alkali-Doped Samarium Oxides", Chemistry Letters, pp. 467–468, 1986.

G. E. Keller et al., "Synthesis of Ethylene via Oxidative Coupling of Methane", Journal of Catalysis, 73, 9–19 (1982).

H. Imai et al., "Oxidative Coupling of Methane over LaAlO$_3$", J. Chem. Soc., Chem. Commun., 1986, pp. 52–53.

K. I. Aika et al., "Oxidative Dimerization of Methane over BaCO$_3$, SrCO$_3$ and these Catalysts promoted with Alkali", J. Chem. Soc., Chem. Commun., 1986, pp. 1210–1211.

K. Otsuka et al., "Selective Synthesis of Ethylene by Partial Oxidation of Methane over LiCl–Sm$_2$O$_3$", J. Chem Soc., Chem. Commun., 1986, pp. 586–587.

Primary Examiner—William R. Dixon, Jr.
Assistant Examiner—James M. Hunter, Jr.
Attorney, Agent, or Firm—A. J. McKillop; C. J. Speciale; E. F. Kenehan, Jr.

[57] ABSTRACT

A method is provided for converting feedstock comprising paraffins by selective oxidative coupling to product comprising higher hydrocarbons including dimers of said feedstock paraffins which comprises contacting said feedstock with a catalyst composition comprising a thermally stable layered metal chalcogenide having adjacent layers separated by chalcogenide pillars, and an alkali metal.

10 Claims, No Drawings

SELECTIVE OXIDATIVE COUPLING

This is a continuation of copending application Ser. No. 128, 124, filed on Dec. 3, 1987 now abandoned.

CROSS-REFERENCE TO RELATED APPLICATION

This application is related by subject matter to application Ser. No. 879,787, filed June 27, 1986, and to application Ser. No. 026,426, filed Mar. 16, 1987 now abandoned each entirely incorporated herein by reference.

BACKGROUND OF THE INVENTION

This invention relates to use of a particular catalyst composition comprising a thermally stable layered metal chalcogenide, such as a titanium oxide, having adjacent layers separated by metal chalcogenide pillars, such as a silicon oxide, and an alkali metal, such as lithium or rubidium, for selective conversion of feedstock comprising $C_n$ paraffins, such as methane, to product comprising $C_{n+1}{}^+$ hydrocarbons plus $C_{2n}$ dimers. For purposes of describing the present invention herein, the term "metal" is considered to include the elements boron, silicon, phosphorus and arsenic.

The conversion of methane into more valuable chemicals has long been a challenge to chemists and engineers alike. Methane is, in general, much more stable than its derivatives. It is especially difficult to selectively oxidize methane without conversion to carbon oxides and water. G. E. Keller et al, *J. of Catal.*, 73, 9–19 (1982) reported converting $CH_4$ to $C_2H_4$ by sequential reaction with pulses of $N_2$, air, $N_2$, etc., to avoid deep oxidation. With Sb, Sn, Mn oxides as catalysts, conversion of less than 10% $CH_4$ has been obtained. T. Ito et al, *J.A.C.S.* 1985, 107, 5062, reported less than 10% conversion of $CH_4$ to $C_2H_4$ using a Li on MgO catalyst. U.S. Pat. No. 4,443,649 teaches that substantial amounts of $C_2H_4$ can be obtained in addition to carbon oxides by contacting methane with Mn oxide on $SiO_2$ at about 800° C. The catalyst aged rapidly (within minutes) due to depletion of oxygen. K. Otsuka et al, *Chem. Lett.* 467 (1986) reported methane oxidation to ethylene and other products over lithium impregnated metal oxides.

Oxidative coupling of methane over $LaAlO_3$ catalyst was reported by H. Imai and T. Tagawa in *J. Chem. Soc., Chem. Commun.*, 52–53 (1986). K. Otsuka, Q. Liu and A. Morikawa reported synthesis of ethylene by partial oxidation of methane over $LiCl-Sm_2O_3$ catalyst to produce $C_2$ compounds, i.e. ethane and ethylene in *J. Chem. Soc., Chem. Commun.*, 586–587 (1986). Oxidative dimerization of methane over $BaCO_3$, $SrCO_3$ and same promoted with alkali was reported by K. Aika et al in *J. Chem. Soc., Chem. Commun.*, 1210–1211 (1986). U.S. Pat. No. 4,574,038 shows a process for converting methane to ethylene and hydrogen over a metal powder catalyst, the methane and catalyst subjected to microwave radiation.

It has now been found that thermally stable layered metal chalcogenides containing metal chalcogenide pillars separating the layers which have been composited with an alkali metal by way of, for example, impregnation with an alkali metal halide, may be employed to selectively convert $C_n$ paraffins to $C_{n+1}{}^+$ hydrocarbon product comprising dimers of the $C_n$ paraffin by the mechanism of oxidative coupling.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other, the interactions between the planes being weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction provided by ions located between the layers. In addition, hydrogen bonding interactions can occur directly between complementary sites on adjacent layers, or can be provided by interlamellar bridging molecules.

Laminated materials such as clays may be modified to increase their surface area. In particular, the distance between the layers can be increased substantially by absorption of various swelling agents such as water, ethylene glycol, amines and, ketones, which enter the interlamellar space and push the layers apart. However, the interlamellar spaces of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing". These values indicate the distance between, for example, the uppermost margin of one layer with the uppermost margin of its adjoining layer. If the layer thickness is known, the interlayer spacing can be determined by subtracting the layer thickness from the basal spacing.

SUMMARY

The present invention resides in a method for selectively converting $C_n$ paraffins to $C_{n+1}{}^+$ hydrocarbons plus the dimers $C_{2n}$, such as follows:

$$xC_n \rightarrow C_{n+1}{}^+ + C_{2n},$$ 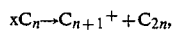

wherein x is greater than 1 and n is greater than or equal to 1, such as, for example, from 1 to 4, which comprises contacting a $C_n$-containing feed with a catalyst composition comprising (1) a thermally stable layered metal chalcogenide having adjacent layers separated by metal chalcogenide pillars and (2) alkali metal at a temperature of from about 400° C. to about 800° C. and a pressure of from about 1 kPa to about 1000 kPa.

Preferably the layered chalcogenide is a layered oxide and most preferably a layered titanate or a layered silicate.

Preferably, the pillars comprise a polymeric oxide and most preferably polymeric silica.

DETAILED DESCRIPTION

The method of the present invention utilizes catalyst prepared from a layered starting material which contains anionic ion exchange sites having interlayer or interspathic cations associated therewith. Such cations may include hydrogen ion, hydronium ion and alkali metal cation. The starting material is treated with a "propping" agent, conveniently comprising a source of an organic cation such as organoammonium ion, in order to affect an exchange of or addition to the interlayer cations and thereby separate the layers of the starting material. For example, where the interlayer cations are hydrogen or hydronium ions, the source of organic cation, may include a neutral compound such as organic amine which is converted to a cationic analogue during the "propping" treatment. The foregoing treatment results in the formation of a layered material of enhanced interlayer separation depending upon the size of the organic cation introduced. In one embodiment, a series of organic cation exchanges is carried out. For example, an organic cation may be exchanged with an organic cation of greater size, thus increasing the interlayer separation in a step-wise fashion. Preferably, contact of the layered material with the propping agent is conducted in aqueous medium so that water is trapped within the interlayer spaces of the propped species.

After the ion exchange, the organic-"propped" species is treated with a compound capable of conversion, preferably by hydrolysis, to a chalcogenide, preferably a polymeric oxide. The "propped" layered material containing the chalcogenide precursor is then treated to produce calcogenide pillars separating the layers. Where the treatment involves hydrolysis, this may for example be carried out using water already present in organic-"propped" layered material.

It is preferred that the organic cation deposited between the layers is capable of being removed from the layered material without substantial disturbance or removal of the chalcogenide pillars or their precursor. For example, organic cations such as n-octylammonium may be removed by calcination or chemical oxidation, although preferably by calcination and preferably after the precursor has been converted to the chalcogenide pillars.

The resulting pillared product exhibits high surface area, e.g. greater than 200, 400, or even 600 $m^2/g$, and thermal stability.

The layered materials used in producing the catalyst employed in the present invention are layered chalcogenides, preferably oxides, of elements having an atomic number from 13 to 15, 21, to 33, 39 to 51, 57 to 83 or greater than 90. Preferably, the layered oxide is "non-swellable" which is intended to distinguish from conventional clays which contain octahedrally coordinated metal oxide sheets bonded to tetrahedrally coordinated silica sheets and which undergo substantial swelling, sometimes by an essentially unbounded amount, when contacted with water. As used herein in relation to a layered oxide material, the term "non-swellable" is defined as meaning a layered oxide material which, when contacted with at least 10 grams of water per gram of the layered oxide at 23° C. for 24 hours, exhibits an increase in d-spacing no greater than 5 Angstrom as compared with the anhydrous material. Included among these materials are $H_2Ti_3O_7$, $Na_2Ti_3O_7$ and $KTiNbO_5$ as well as certain layered perovskites, titanometallates and silicates, for example, the metasilicates magadiite, natrosilite, kenyaite, makatite and kanemite. Other suitable starting materials include layered clays, such as bentonite, although these are swellable in water. With certain layered starting materials, for example layered silicates, it has been found to be preferable to treat the siliate with one or more polar solvents prior to or during exchange with the source of organic cation. If an organic polar solvent is used, it should exhibit an electric dipole moment in the gas phase of at least 3.0 Debyes (D), preferably at least 3.5 D, most preferably at least about 3.8D. Examples of suitable solvents are water, dimethylsulfoxide (DMSO) and dimethylformamide (DMF). A table of selected organic compounds and their electric dipole moments can be found in *CRC Handbook of Chemistry and Physics*, 61st Edition, 1980–1981 at pages E-64 to E-66. It is believed that the treatment of the oxide starting material with one or more highly polar solvents facilitates the introduction of the source of organic cation between the layers of the starting material.

In one preferred embodiment, the starting material is a layered metal oxide of Group IVB (Periodic Table of the Elements) metal such as titanium, zirconium and hafnium, with a layered titanate, e.g. a trititanate such as $Na_2Ti_3O_7$, being particularly preferred. Trititanates are commercially available materials whose structure consists of anionic sheets of titanium octahedra with interlayer alkali metal cations. A method for making such material may be found in U.S. Pat. No. 2,496,993. In another preferred embodiment the starting material is a layered silicate having the structure of magadiite.

As previously stated, the layered starting material is treated with an organic compound capable of forming cationic species such as organophosphonium, organoammonium or organic amines, before introduction of the pillar material. Insertion of the organic cation between the adjoining layers serves to physically separate the layers in such a way as to make the layered oxide receptive to the interlayer addition of an electrically neutral, hydrolyzable, chalcogenide precursor. In particular, alkylamines, such as n-octylamine, have been found useful in the present invention. Thus $C_3$ and larger alkylammonium or alkylamines, e.g. n-octylammonium, cations or n-octylamine, are readily incorporated within the interlayer species of the layered oxides, serving to prop open the layers in such a way as to allow incorporation of the polymeric oxide precursor. The extent of the interlayer spacing can be controlled by the size of the organoammonium ion or organoamine employed so that, with a trititanate as the layered oxide starting material, use of the n-propylammonium cation will achieve an interlayer spacing of 2–5 Angstrom, whereas to achieve an interlayer spacing of 10–20 Angstrom an n-octylammonium cation or a cation of equivalent length is required. Indeed, the size and shape of the organic cation can affect whether or not it can be incorporated within the layered oxide structure at all. For example, bulky cations such as tetrapropylammonium are generally undesirable for use in the present method, whereas n-alkyl ammonium cations, such as those derived from n-alkyl primary amines and $R_3R'N^+$ cations, were R is methyl or ethyl and R' is an alkyl group with at least 5 carbon atoms, are preferred. The organic ammonium cations separating the oxide layers may be formed in situ by reaction of the neutral amine species with interlayer hydrogen or hydronium cations of the layered starting material. Alternatively where the interlayer cations of the layered starting material are alkali metal cations, the organic ammonium cation may be formed by initially combining an amine and an aqueous acid solution, such as hydrochloric acid, and then treating the layered oxide with the resulting aqueous organoammonium ion solution. In either case, the treatment is conducted in aqueous media so that water is then available to hydrolyze the electrically neutral, hydrolyzable polymeric oxide precursor subsequently introduced into the "propped" product.

The chalcogenide pillars formed between the layers of the oxide starting material preferably comprise an oxide, and more preferbly comprise a polymeric oxide, of at least one element selected from Groups IB, IIB, IIIA, IIIB, IVA, IVB, VA, VB, VIB, VIIB, and VIII of the Periodic Table of Elements (Sargent-Welch Scientific Company). In one preferred embodiment, the pillars comprise an oxide of zirconium, titanium or more preferably of at least one element selected from Group IVA of the Periodic Table, other than carbon, and most preferably include polymeric silica. Where the layered starting material is a silicate, such as magadiite, the pillars preferably comprise polymeric silica and alumina. The polymeric oxide pillars are formed from a precursor material which is preferably introduced between the layers of the organic propped species as a cationic, or more preferably electrically neutral, hydrolyzable compound of the desired element(s).

The precursor material is preferably an organometallic compound which is a liquid under ambient conditions. Suitable polymeric silica precursor materials include tetrapropylorthosilicate, tetramethylorthosilicate and, most preferably, tetraethylorthosilicate. Where the pillars are also required to include polymeric alumina a hydrolyzable aluminum compound can be contacted with the organic "propped" species before, after or simultaneously with the contacting of the layered starting material with the silicon compound. Preferably, the hydrolyzable aluminum compound employed is an aluminum alkoxide, e.g. aluminum isopropoxide.

After hydrolysis to produce the polymeric oxide pillars and calcination to remove the organic propping agent, the final pillared product may contain residual exchangeable cations. For example, sodium titanate pillared with polymeric silica may contain 2-3% of weight of residual sodium. Such residual cations can be ion exchanged by methods well known with other cationic species to provide or alter the catalytic activity of the pillared product.

In one preferred embodiment, where the layered starting material is a titanate and the pillars are formed of silica, the resulting silicotitanate product exhibits the characteristic X-ray diffraction pattern shown in Table 1 below.

TABLE 1

| Line Number | Composite List of Principal X-Ray Powder* Diffraction Peaks For Silicotitanates | |
|---|---|---|
| | (2 Theta-2 Theta) (Minimum Maximum) | 100 $I/I_o$ (Relative Intensity) Range |
| 1 | less than or equal to 8.7 | VS to W |
| 2 | 11.1-14.3 | S to W |
| 3 | 11.8-15.2 | M to W |
| 4 | 24.5-25.0 | VS to W |
| 5 | 25.0-25.4 | M to W |
| 6 | 28.5-30.2 | VS to W |
| 7 | 29.8-30.6 | S to W |
| 8 | 33.0-33.5 | S to W |
| 9 | 43.2-43.5 | M to W |

TABLE 1-continued

| Line Number | Composite List of Principal X-Ray Powder* Diffraction Peaks For Silicotitanates | |
|---|---|---|
| | (2 Theta-2 Theta) (Minimum Maximum) | 100 $I/I_o$ (Relative Intensity) Range |
| 10 | 44.2-44.7 | M to W |
| 11 | 48.5-48.9 | VS to M |
| 12 | 52.7-52.9 | W |

*2 Theta minimum - 2 Theta maximum = Range of 2 Theta-values observed for eight specific pillared silicotitanates These values were determined by standard techniques. The radiation was the K-alpha doublet of copper, and a scintillation counter spectrometer was used. The peak heights, I, and the positions as a function of 2 times theta, where theta is the Bragg angle, were determined. From these, the relative intensities, $I/I_o$ where $I_o$ is the intensity of the strongest line or peak, and d is the interplanar spacing in angstroms (A), corresponding to the recorded lines, were calculated. The relative intensity in the table above is expressed as follows:

| Relative Intensity | 100 I/Io |
|---|---|
| VS (Very Strong) | 60-100 |
| S (Strong) | 40-60 |
| M (Medium) | 20-40 |
| W (Weak) | 0-20 |

Variations in the interplanar spacing and relative intensity may occur as a result of ion exchange, changes in the composition of the silicotitanate, or exposure to calcination conditions.

Prior to use as a catalyst in the present process, the pillared chalcogenide, e.g. titanate, material must be composited with a Periodic Table group IA element, such as, for example Li, Rb or a combination thereof. The alkali metal is added to the pillared, layered chalcogenide by impregnation with the salt thereof, such as for example, the halide salt. Non-limiting examples of such materials include LiCl, LiBr, RbCl and RbBr.

Layered silicates employed in the present invention may be high silica alkali silicates whose layers lack octahedral sheets and which are prepared hydrothermally from aqueous reaction mixture containing silica and caustic at relatively moderate temperatures and pressures. The layered silicates may contain tetracoordinate framework atoms other than Si in the layers which can be introduced by co-crystallizing in the presence of non-silicon tetravalent elements, e.g. those selected from the group consisting of Al, B, Co, Cr, Fe, Ga, In, Ni, Zr as well as any other such elements which are catalytically useful when incorporated in the silicate structure. Alternatively, non-silicon framework elements already in a layered silicate may be substituted by a different tetracoordinate element. For example, kenyaite containing boron in its framework when treated with aluminum nitrate results in a kenyaite which contains aluminum in its framework. Both co-crystallized and substituted layered high silica alkali silicates may be treated to provide layered materials containing interspathic oxide pillars.

One such layered silicate is synthetic substituted magadiite. Synthetic magadiite is readily produced hydrothermally from a reaction mixture containing inexpensive sources of silica and caustic. Tetracoordinate elements X other than silicon, e.g. Al, B, Co, Cr, Fe, Ga, In, Ni, Zr, preferably Al or Fe, may be added to the reaction mixture as may a suitable organic directing agent R. The reaction mixture for such synthetic magadiite-type materials can be described in molar ratios as follows:

$SiO_2/X_2O_3 = 10$ to infinity where X can be Al, B, Co, Cr, Fe, Ga, and/or Ni or other catalytically useful metal $M^+OH^-/SiO_2 = 0$ to 0.6, (preferably 0.1–0.6) M = any alkali metal $H_2O/SiO_2 = 8–500$ $R/SiO_2 = 0–1.0$ where R can be an organic such as benzyltriethylammonium chloride, benzyltrimethylammonium chloride, dibenzyldimethylammonium chloride, N,N'-dimethylpiperazine, triethylamine, or other quaternary compounds or heterocyclic amines.

The reaction mixture is maintained at a temperature of 100° to 200° C. for anywhere from 1 to 150 days in order to form a product having the following composition:

%N = 0–3, e.g. 0 to 0.3

$SiO_2/X_2O_3 = 10$ to infinity where X is in the tetrahedral or octahedral position $M_2O/SiO_2 = 0$ to 0.5, e.g. 0.05–0.1

The synthetic layered silcate material thus prepared is of low surface area. Introduction of interspathic polymeric oxides according to the method of the present invention can increase the surface area of the material. Generally, the synthetic magadiite-type material is acidified by any suitable means, e.g. treatment with aqueous 0.1N HCl, before being treated with a "propping" agent, alone or combined with a suitable polar solvent.

The process of this invention is conveniently carried out in the vapor-phase by contacting the $C_n$ paraffin feed in a reaction zone, such as, for example, a fixed bed of catalyst composition, under conversion effective conditions including a temperature of from about 400° C. to about 800° C., preferably from about 500° C. to about 750° C., and a pressure of from about 1 kPa to about 1000 kPa, preferably from about 1 kPa to about 100 kPa. The gas hourly space velocity (GHSV) may be maintained at from about 100 hr$^{-1}$ to about 6000 hr$^{-1}$, preferably from about 200 hr$^{-1}$ to about 3000 hr$^{-1}$. This process may be conducted in either batch or fluid bed operation with attendant benefits of either operation readily obtainable.

As mentioned above, feedstock compounds to be converted hereby include $C_n$ paraffins, and product will comprise $C_{n+1}$ and higher hydrocarbons plus $C_{2n}$ dimers. A preferred product component will include olefinic dimers of the $C_n$ paraffins. Non-limiting examples of the feedstock and respective product components are:

| $C_n$ | $C_{n+1}^+$ | $C_{2n}$ |
|---|---|---|
| methane | $C_2^+$, e.g. ethylene | $C_2$, e.g. ethylene |
| ethane | $C_3^+$, e.g. propylene | $C_4$, e.g. butylene |
| propane | $C_4^+$, e.g. butylene | $C_6$, e.g. hexene |
| butane | $C_5^+$, e.g. pentene | $C_8$, e.g. octene |

The present invention is illustrated further by the following examples.

EXAMPLE 1

A mixture of 900 g $Na_2Ti_3O_7$, 770 g n-octylamine, 559 g 37.8% HCl and 5 liters of water was refluxed for 22 hours. The solution was cooled to 70° C. and 281 g of 37.8% HCl was added. The product was filtered, washed with 10 liters hot water, and dried 20 hours at room temperature. The solid product was stirred in 3 liters absolute ethanol at room temperature for one hour, filtered, and air-dried at room temperature for 24 hours. The air-dried material was then stirred in 4 liters water at room temperature for 23 hours, filtered, and dried for 24 hours at room temperature.

An 825 g portion of the dried product was mechanically stirred in 5.5 kg of tetraethylorthosilicate in a 10 liter beaker covered with perforated aluminum foil for 68 hours at room temperature and then filtered and dried in air at room temperature for about 4 days. This material was calcined in nitrogen at 950° C. for two hours and then in air for one hour at 950° F. The product proved to be a silicotitanate with a surface area of 299 m$^2$/g and the following composition (wt.%):

| $TiO_2$ | 70.2 |
|---|---|
| $SiO_2$ | 21.7 |
| Na | 3.3 |
| Ash | 100.0 |

EXAMPLE 2

Ten parts of the product from Example 1 were impregnated with a solution of 1.4 parts of LiCl and sufficient water to moisten the entire sample to incipient wetness. The product was then dried, sized and calcined at 700° C. in air for two hours.

EXAMPLE 3

A RbCl impregnated silicotitanate was prepared by the same procedure as in Example 2, except 4.2 parts of RbCl were used.

EXAMPLE 4

LiCl impregnated $TiO_2$ (anatase) and $MnO_2$ (activated) were prepared by the same procedure as in Example 2 but with the following compositions:

A. Ten parts $TiO_2$ + 1.31 parts of LiCl

B. Ten parts $MnO_2$ + 1.21 parts of LiCl

EXAMPLE 5

RbCl impregnated $TiO_2$ (anatase) and $MnO_2$ (activated) were prepared by the same procedure as in Example 2 but with the following compositions:

A. Ten parts $TiO_2$ + 3.8 parts RbCl

B. Ten parts $MnO_2$ + 3.5 parts RbCl

EXAMPLE 6

The product compositions of Examples 1–5 were compared for methane conversion by oxidative coupling to higher hydrocarbons. The catalysts were each placed in turn into a ⅜-inch I.D. glass reactor fitted with an imbedded thermocouple. In each test, for 1 g of catalyst the feedstock rates were adjusted to be 5 ml/min $CH_4$, 10 ml/min air and 85 ml/min $N_2$. Reactor temperatures were varied and product analyses were done by on-line gas chromatography at 30 minute intervals. Table 2 presents the test results.

TABLE 2

| Catalyst Preparation | Example 2 | | Example 3 | | Example 4A | | Example 4B | | Example 5A | | Example 5B | |
|---|---|---|---|---|---|---|---|---|---|---|---|---|
| Test Temperature, °C. | 704 | 706 | 649 | 704 | 732 | 760 | 732 | 760 | 649 | 704 | 649 | 704 |
| $CH_4$ Conv., % | 42.4 | 50 | 29.9 | 36.9 | 31.2 | 33.6 | 39.8 | 41.0 | 15.3 | 20.3 | 14.6 | 23.2 |
| Hydrocarbon Selectivity, % | 75 | 89 | 6 | 21 | 55 | 60 | 79 | 82 | 5.9 | 31 | 1.4 | 1.3 |
| Product Distribution, % | | | | | | | | | | | | |
| Ethylene | 29.2 | 39.5 | 1.4 | 3.8 | 16.7 | 19.9 | 26.2 | 28.0 | — | 2.6 | — | — |
| Ethane | — | — | — | 3.6 | — | — | — | — | 0.9 | 3.7 | — | 0.3 |
| $C_3$'s | 0.3 | 0.9 | — | — | — | — | 0.6 | 0.6 | — | — | — | — |
| $C_4$'s | 0.9 | 1.8 | — | — | — | — | 1.4 | 1.3 | — | — | — | — |
| Benzene | 0.8 | 1.1 | — | — | — | — | 1.8 | 2.2 | — | — | — | — |
| Toluene | 0.5 | 1.0 | 0.3 | 0.3 | 0.4 | 0.2 | 1.4 | 1.6 | — | — | 0.2 | — |
| $CO + CO_2$ | 10.7 | 5.5 | 28.1 | 29.2 | 14.1 | 13.5 | 8.4 | 7.3 | 14.4 | 14.0 | 14.4 | 22.9 |

Comparison of the Example 6 results leads to the conclusion that the present process with a catalyst composition of (1) thermally stable layered metal chalcogenide having adjacent layers separated by metal chalcogenide pillars, e.g. a silicotitanate and (2) an alkali metal, e.g. lithium or rubidium, outperforms such a process with a catalyst of lithium/titanate, lithium/manganate, rubidium/titanate or rubidium/manganate. The Example 2 product catalyst converted 42.4% and 50% of the methane at 704° C. and 760° C., respectively, compared to 31.2% at 732° C. and 33.6% at 760° C. for the Example 4A product catalyst, and 39.8% at 732° C. and 41% at 760° C. for the Example 4B product catalyst, respectively. The Example 3 product catalyst converted 29.9% and 36.9% of the methane at 649° C. and 704° C., respectively, compared to 15.3% at 649° C. and 20.3% at 704° C., respectively, for the Example 5A product catalyst, and 14.6% at 649° C. and 23.2% at 704° C. for the Example 5B product catalyst, respectively.

Further, the Example 2 and 3 product catalysts provided more ethylene than the Example 4A, 4B, 5A and 5B product catalysts.

What is claimed is:

1. A process for converting feedstock comprising methane into a product comprising $C_2+$ hydrocarbons including ethylene which comprises contacting said feedstock at conversion conditions including a temperature of from about 400° C. to about 800° C., a pressure of from about 1 kPa to about 1000 kPa and a gas hourly space velocity of from about 100 $hr^{-1}$ to about 6000 $hr^{-1}$ with a catalyst composition comprising layered titanate having adjacent layers separated by silica pillars, said catalyst composition further comprising an alkali metal.

2. The process of the claim 1 wherein said layered silica having adjacent layers separated by silica pillers comprises a silicotitanate having a characteristic X-ray diffraction pattern substantially as shown in Table 1.

3. A process for converting feedstock comprising methane into a product comprising $C_2+$ hydrocarbons including ethylene, said process comprising contacting said feedstock at conversion conditions including a temperature of from about 400° C. to about 800° C., a pressure of from about 1 kPa to about 1000 kPa and a gas hourly space velocity of from about 100 $hr^{-1}$ to about 6000 $hr^{-1}$ with a catalyst composition comprising (1) layered metal chalcogenide having adjacent layers separated by chalcogenide pillars, said catalyst composition further comprising (2) one or more alkali metals.

4. The process of claim 3 wherein said layered metal chalcogenide comprises an oxide.

5. The process of claim 4 wherein said oxide comprises titanate or silicate.

6. The process of claim 3 wherein said pillars comprise an oxide of at least one element selected from the group consisting of Periodic Table of Elements Groups IB, IIB, IIIA, IIIB, IVA, IVB, VA, VB, VIB, VIIB and VIII.

7. The process of claim 6 wherein said oxide comprises a polymeric oxide.

8. The process of claim 6 wherein said element comprises silicon.

9. The process of claim 3 wherein said layered chalcogenide comprises layered titanate and said pillars comprise silica.

10. The process of claim 3 wherein said conversion conditions include a temperature of from about 400° C. to about 800° C., a pressure of from about 1 kPa to about 1000 kPa and a gas hourly spaced velocity of from about 100 $hr^{-1}$ to about 6000 $hr^{-1}$.

* * * * *